US007656533B2

(12) United States Patent
Kang et al.

(10) Patent No.: US 7,656,533 B2

(45) Date of Patent: Feb. 2, 2010

(54) FLOWING DEVICE FOR OPTICS-BASED METHANOL SENSOR

(75) Inventors: Sang-kyun Kang, Yongin-si (KR); Dong-kee Sohn, Yongin-si (KR); Woong-ho Cho, Yongin-si (KR); Sang-hyeon Choi, Yongin-si (KR); Seok-rak Chang, Yongin-si (KR)

(73) Assignee: Samsung SDI Co., Ltd., Suwon-si (KR)

( * ) Notice: Subject to any disclaimer, the term of this patent is extended or adjusted under 35 U.S.C. 154(b) by 204 days.

(21) Appl. No.: 11/641,861

(22) Filed: Dec. 20, 2006

(65) Prior Publication Data

US 2007/0261485 A1 Nov. 15, 2007

(30) Foreign Application Priority Data

May 15, 2006 (KR) ..................... 10-2006-0043461

(51) Int. Cl.
*G01N 21/00* (2006.01)

(52) U.S. Cl. ..................................................... 356/436

(58) Field of Classification Search ................. 356/445, 356/446, 136, 135, 128

See application file for complete search history.

(56) References Cited

U.S. PATENT DOCUMENTS

| | | | | |
|---|---|---|---|---|
| 4,974,552 | A * | 12/1990 | Sickafus | 123/1 A |
| 5,074,659 | A * | 12/1991 | Suzuki et al. | 356/135 |
| 5,110,205 | A * | 5/1992 | Suzuki et al. | 356/135 |
| 5,157,453 | A * | 10/1992 | Suzuki et al. | 356/128 |
| 5,898,503 | A | 4/1999 | Keller et al. | |
| 5,971,609 | A * | 10/1999 | Kijima et al. | 374/17 |
| 6,183,696 | B1 | 2/2001 | Elkind et al. | |
| 2003/0121865 | A1* | 7/2003 | Winn et al. | 210/739 |

FOREIGN PATENT DOCUMENTS

| | | |
|---|---|---|
| CN | 2423583 Y | 3/2001 |
| CN | 2511978 Y | 9/2002 |
| JP | 4-278442 | 10/1992 |

OTHER PUBLICATIONS

Office Action issued by Chinese Patent Office in Chinese Patent Application No. 2007100021309 on Feb. 6, 2009.

Office Action issued by the Japanese Patent Office in Japanese Patent Application No. 2007-102116 on Mar. 31, 2009.

* cited by examiner

*Primary Examiner*—Tarifur R. Chowdhury
*Assistant Examiner*—Isiaka O Akanbi
(74) *Attorney, Agent, or Firm*—Stein McEwen, LLP

(57) ABSTRACT

A flowing device for an optics-based methanol sensor includes an inner housing that surrounds the optics-based methanol sensor, an outer housing that surrounds the inner housing, a flow channel in the inner housing formed on a totally reflecting surface of the optics-based methanol sensor, a fuel inlet that is formed through the inner and outer housings and supplies liquid fuel to the flow channel, and a fuel outlet that is formed through the inner and outer housings and discharges the liquid fuel that has passed through the flow channel to an outside of the outer housing.

19 Claims, 6 Drawing Sheets

20
14
60
10
112
114
170
13
11
110

FLOWING DEVICE FOR OPTICS-BASED METHANOL SENSOR

CROSS-REFERENCE TO RELATED APPLICATIONS

This application claims the benefit of Korean Patent Application No. 2006-43461, filed on May 15, 2006, in the Korean Intellectual Property Office, the disclosure of which is incorporated herein in its entirety by reference.

BACKGROUND OF THE INVENTION

1. Field of the Invention

Aspects of the present invention relate to a flowing device for an optics-based methanol sensor, and more particularly, to a flowing device that supplies methanol to an optics-based methanol sensor that optically measures the concentration of methanol.

2. Description of the Related Art

Direct liquid feed fuel cells mainly use methanol as fuel. When a high concentration of methanol is supplied to an anode of a direct liquid feed fuel cell, the efficiency of the fuel cell in terms of electricity generation is greatly reduced due to cross-over of fuel through the electrolyte membrane (hydrogen ion exchange membrane) from the anode to the cathode. Therefore, diluted methanol with a concentration of 0.5 to 2M (2 to 8 vol. %) is generally used.

A direct liquid feed fuel cell system includes a fuel tank where methanol in a high concentration or pure methanol is stored. A diluted fuel having a uniform concentration and made by mixing the methanol from the fuel tank with water, such as recovered water or water from a water tank, is supplied to an anode electrode. A methanol sensor for detecting the concentration of the mixed fuel is desirable.

An optics-based sensor having a interior flow channel that supplies a sample to the optics-based sensor has been disclosed in U.S. Pat. No. 6,183,696. However, the flow channel can interfere with an optical path of the sensor, and the inner structure of the sensor is complicated.

SUMMARY OF THE INVENTION

Aspects of the present invention provide a flow channel that contacts an outer surface of an optics-based liquid fuel sensor, such as an optics-based methanol sensor and a flowing device that increases the reliability of the optics-based liquid fuel sensor.

According to an aspect of the present invention, there is provided a flowing device for an optics-based liquid fuel sensor comprising: an inner housing that surrounds the optics-based liquid fuel sensor; an outer housing that surrounds the inner housing; a flow channel in the inner housing formed on a totally reflecting surface of the optics-based liquid fuel sensor; a fuel inlet that is formed through the inner and outer housings and supplies liquid fuel to the flow channel; and a fuel outlet that is formed through the inner and outer housings and discharges the liquid fuel that has passed through the flow channel to an outside of the outer housing.

The inner housing may comprise a flow path between the flow channel and the fuel outlet so that the liquid fuel can contact a surface of the optics-based liquid fuel sensor.

The flow path may be a serpentine groove.

The inner housing may be formed of a material having a higher thermal conductivity than a material of a main body of the optics-based liquid fuel sensor, and the outer housing may be formed of a material having a lower thermal conductivity than a material of the main body of the optics-based liquid fuel sensor.

The flow channel may accommodate a liquid fuel having a flow speed of 15 to 40 cm/sec.

According to another aspect of the present invention, there is provided a flowing device for an optics-based liquid fuel sensor comprising: a housing that surrounds the optics-based liquid fuel sensor; a flow guide that is disposed between the housing and the optics-based liquid fuel sensor, and comprises a flow channel formed on a totally reflecting surface of the optics-based liquid fuel sensor and an opening to guide liquid fuel passing through the flow channel to contact a first side surface of the optics-based liquid fuel sensor; a fuel inlet that is formed through the inner and outer housings and supplies liquid fuel to the flow channel; and a fuel outlet that is formed through the inner and outer housings and discharges the liquid fuel that has passed through the flow channel to the outside of the outer housing The flowing device may further comprise a discharge flow line installed between the housing and a second side surface opposite to the first side surface of the optics-based methanol sensor, wherein the liquid fuel that has passed through the opening of the flow guide moves to the fuel outlet through the discharge flow channel.

The flow channel may be a groove formed on the flow guide to contact the totally reflecting surface.

According to another aspect of the present invention, there is provided an optics-based liquid fuel sensor system comprising: an optics-based liquid fuel sensor and one of the flowing devices described above.

According to another aspect of the present invention, there is provided a direct liquid feed fuel cell system comprising: a direct liquid feed fuel cell and an optics-based liquid fuel sensor system that determines a concentration of liquid fuel entering the direct liquid feed fuel cell, wherein the optics-based liquid fuel sensor system comprises an optics-based liquid fuel sensor and one of the flowing devices described above.

According to another aspect of the present invention, there is provided a method of determining a concentration of a liquid fuel in a water/liquid fuel mixture comprising: directing the water/liquid fuel mixture along a flow channel formed on a totally reflecting surface of an optics-based liquid fuel sensor at a flow speed sufficient to inhibit an accumulation of bubbles in the flow channel, while irradiating the totally reflecting surface with light and determining a concentration of light reflected from the totally reflecting surface, and directing the water/liquid fuel mixture along a flow path whereby the water/liquid fuel mixture contacts at least one structural surface of the optics-based liquid fuel sensor so as to equilibrate a temperature of the totally reflecting surface of the optics-based liquid fuel sensor and the at least one structural surface of the optics-based liquid fuel sensor.

Additional aspects and/or advantages of the invention will be set forth in part in the description which follows and, in part, will be obvious from the description, or may be learned by practice of the invention.

BRIEF DESCRIPTION OF THE DRAWINGS

These and/or other aspects and advantages of the invention will become apparent and readily appreciated from the following description of the embodiments, taken in conjunction with the accompanying drawings of which.

DETAILED DESCRIPTION OF THE EMBODIMENTS

Figure 1:
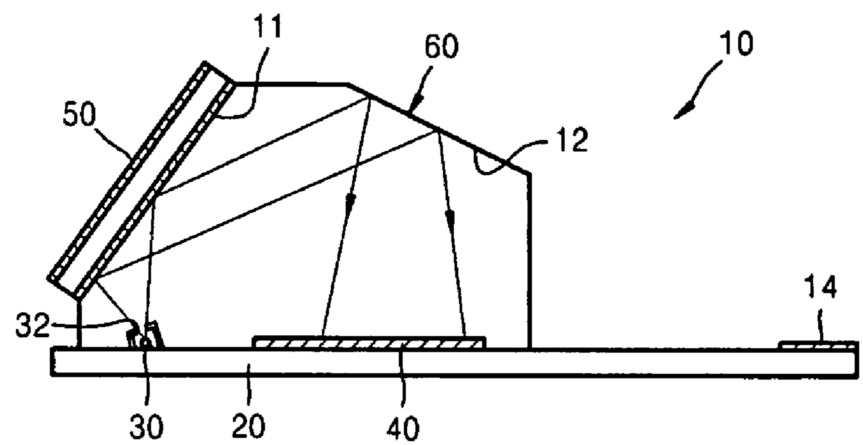
FIG. 1 is a cross-sectional view showing the components of an optics-based methanol sensor. The flowing device according to aspects of the present invention can be used with the optics-based methanol sensor.

Reference will now be made in detail to the present embodiments of the present invention, examples of which are illustrated in the accompanying drawings, wherein like reference numerals refer to the like elements throughout. The embodiments are described below in order to explain the present invention by referring to the figures.

FIG. 1 is a cross-sectional view of an optics-based methanol sensor such as can be used with a flowing device according to an embodiment of the present invention. The optics-based methanol sensor 10 may be similar to an optics-based sensor disclosed in U.S. Pat. Nos. 5,898,503 and 6,183,696 or a refractive index sensor of Texas Instruments.

Referring to FIG. 1, a light emitting unit 30 and a light receiving unit 40 are formed on a base plate 20. An aperture 32 is formed in front of the light emitting unit 30 so that light can be dispersed at a predetermined angular range from the light emitting unit 30. A sensor 10 includes a first surface 11 into which light enters and a second surface 12 that changes an optical path of light totally reflected at the first surface 11. The light reflected at the second surface 12 enters the light receiving unit 40. Reference numeral 50 denotes a flow channel that is formed to contact the first surface 11. The quantity (or angular range) of light totally reflected at the first surface 11 changes according to the concentration of the methanol in the flow channel, and thus, the irradiation range of light at the light receiving unit 40 is changed. Reference numeral 14 denotes a metal line that is electrically connected to the light emitting unit 30 and the light receiving unit 40 so as to supply power to, and output signals from, the sensor 10.

The light emitting unit 30 may be a light emitting diode (LED), and the light receiving unit 40 may be a photodiode array. It is to be understood that in an optics-based methanol sensor used with the flowing device according to aspects of the present invention, other types of light emitting units and light receiving units may be used. The concentration of methanol in the flow channel 50 can be detected by measuring the quantity of light that is totally reflected at the first surface 11.

The refractive index of the methanol fuel widely varies according to its temperature. Accordingly, the refractive index is very sensitive to the temperature of fuel containing methanol in a direct liquid feed fuel cell whose temperature is higher than atmospheric temperature by 30 to 50° C. Also, a light receiving region in the light receiving unit 40 can be distorted due to the non-uniform thermal deformation of a sensor main body 60, such as, for example, a sensor main body formed of a plastic, and such distortion can cause an error in measuring the concentration of methanol.

Also, when the flow speed of a liquid fuel that contains methanol is too slow in the flow channel 50, bubbles may accumulate in the flow channel 50 where the flow channel 50 contacts the first surface 11. The bubbles can cause an incorrect measurement of the methanol sensor 10 by changing the intensity of reflecting light.

Accordingly, when applying the optics-based methanol sensor 10 to a direct liquid feed fuel cell, maintaining a uniform temperature of the sensor main body 60 and a flow speed of the liquid fuel greater than a predetermined speed in a region where the optics-based methanol sensor 10 contacts the liquid fuel (that is, in the flow channel 50) are desirable.

Although aspects of the present invention are described in terms of a methanol sensor, it is to be understood that the sensor having the flowing device according to aspects of the present invention is not limited to a methanol sensor and may generally be any optics based sensor for liquid fuel.

Figure 2:
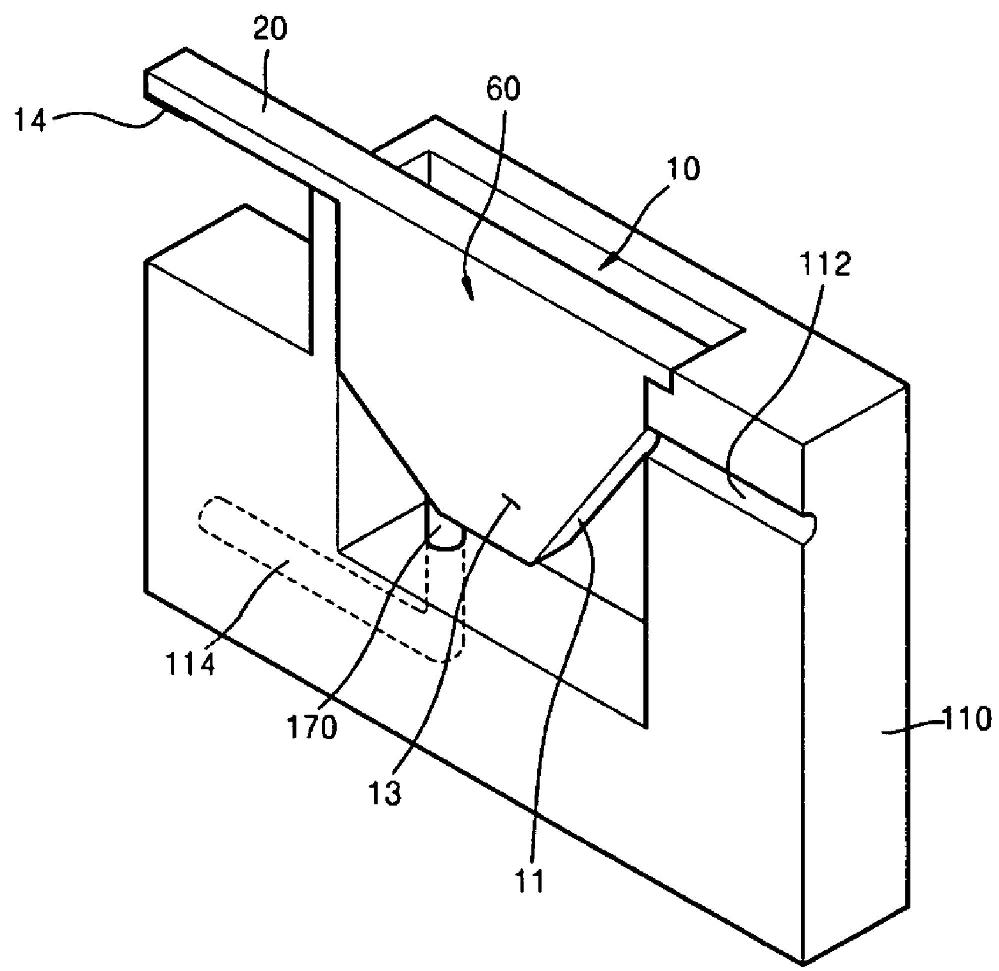
FIG. 2 is a partial perspective view of a flowing device for an optics-based methanol sensor according to an embodiment of the present invention.
Figure 3A:
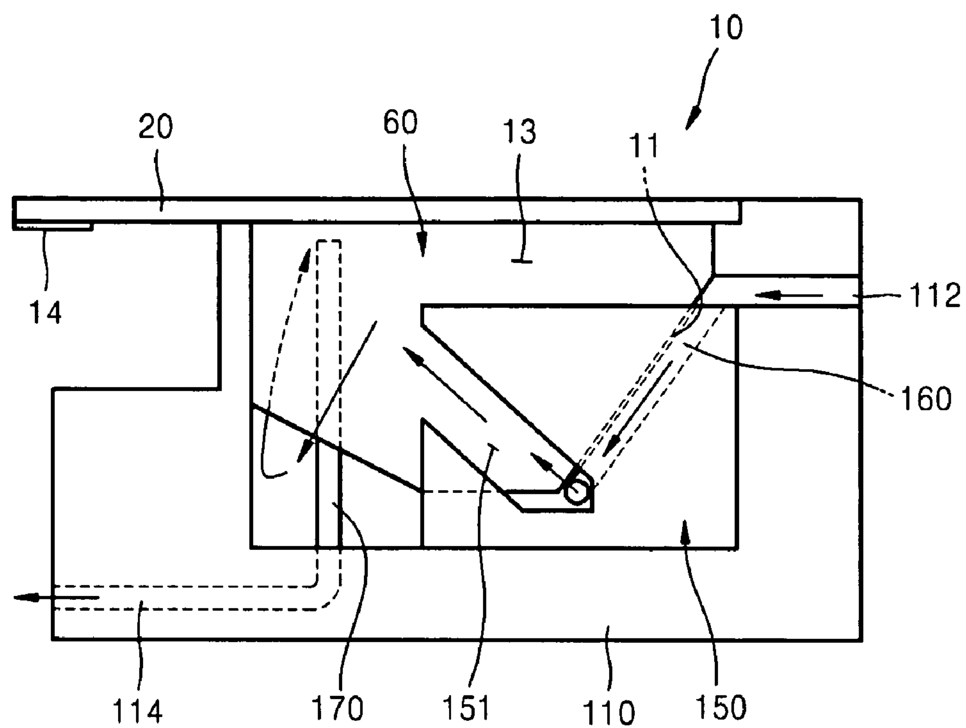
FIGS. 3A and 3B are cross-sectional views illustrating an operation of the flowing device of FIG. 2.
Figure 3B:
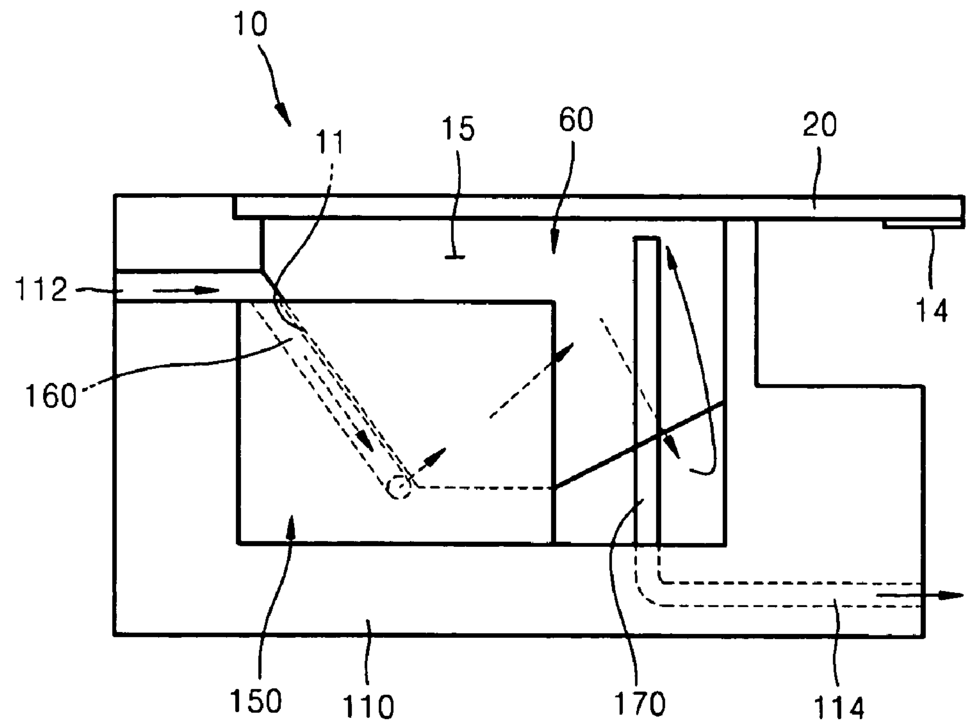
Figure 4:
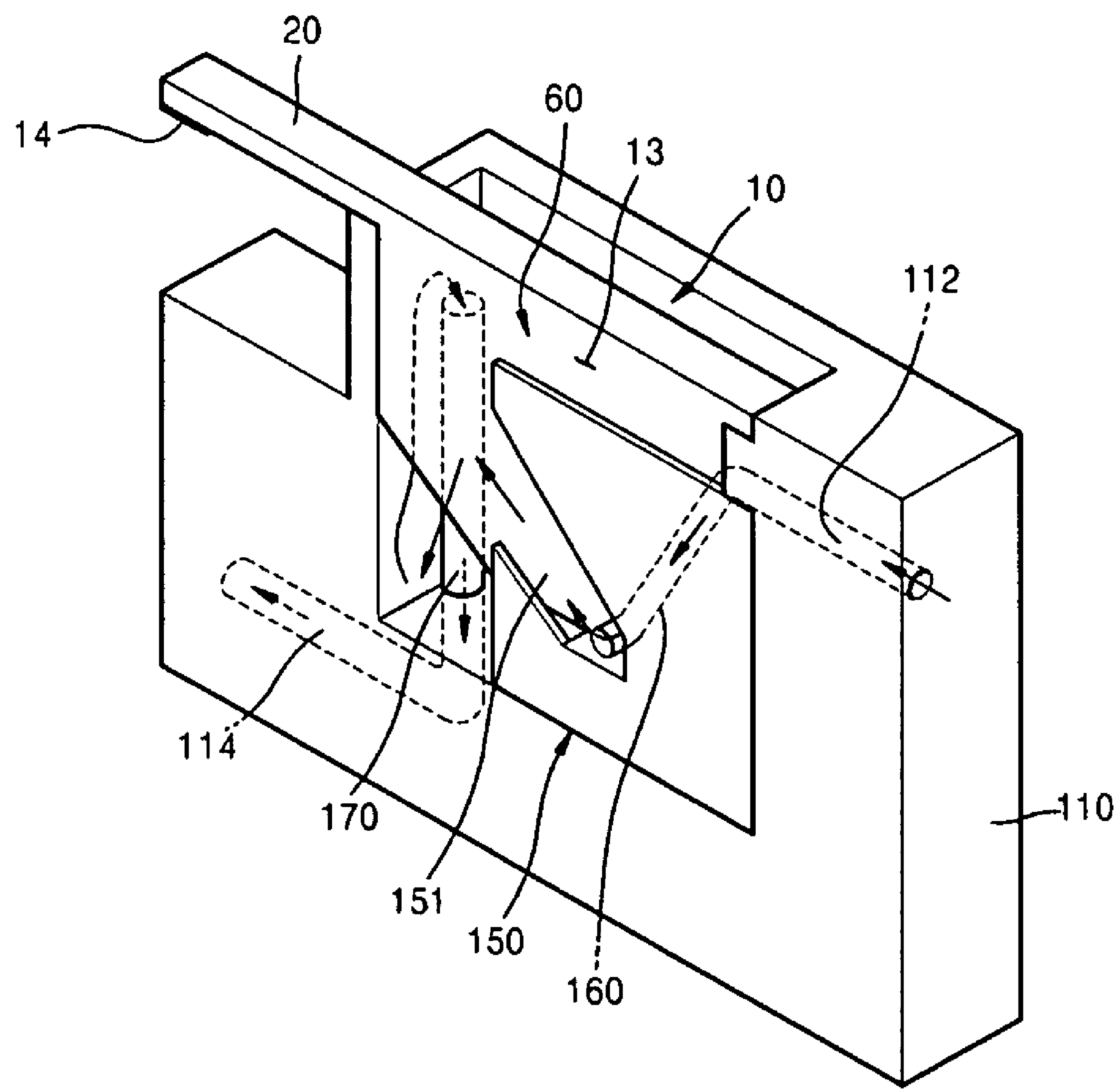
FIG. 4 is a perspective view illustrating an operation of the flowing device of FIG. 2.
Figure 5:
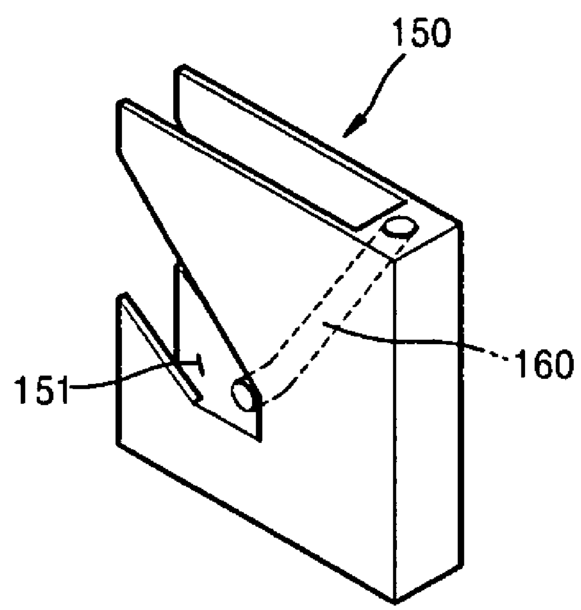
FIG. 5 is a perspective view of the flow guide of the flowing device of FIG. 2.

FIG. 2 is a partial perspective view of a flowing device for an optics-based methanol sensor according to an embodiment of the present invention. (For clarity, the flow guide is not shown in FIG. 2.) FIGS. 3A and 3B are cross-sectional views illustrating an operation of the flowing device according to the same embodiment as FIG. 2, and FIG. 4 is a perspective view illustrating an operation of the flowing device according to the same embodiment as FIG. 2. FIG. 4 shows the combination of the flow guide and the optics-based methanol sensor. FIG. 5 is a perspective view of the flow guide of the flowing device according to the same embodiment as FIG. 2. Like reference numerals in FIGS. 2 through 5 denote like elements in FIG. 1, and thus the detailed descriptions thereof are omitted.

According to the embodiment of FIGS. 2 through 5, a methanol sensor 10 is installed on an upper part of a housing 110 exposing the base plate 20 of the methanol sensor 10 and the metal line 14. A flow guide 150 and a discharge flow line 170 are formed between the housing 110 and the methanol sensor 10. The housing 110 includes a fuel inlet 112 through which a liquid fuel enters and a fuel outlet 114 through which the liquid fuel exits.

The flow guide 150 includes a flow channel 160 connected to the fuel inlet 112 for passing a liquid fuel and an opening 151 connected to a lower end of the flow channel 160. The flow channel 160 may be formed as a long pipe, and also can be formed as a groove (not shown) facing the first surface 11 of the methanol sensor 10. When the flow channel 160 is formed in the groove, the liquid fuel can contact the first surface 11 while flowing through the groove.

The flow channel 160 is mainly formed in a lengthwise direction with respect to the first surface 11. Liquid fuel that has passed through a lower end of the flow channel 160 then contacts a first side surface 13 through the opening 151 formed between the first side surface 13 of the sensor main body 60 and the housing 110.

A lower end of the discharge flow line 170 is connected to the fuel outlet 114. The discharge flow line 170 is installed on a second side surface 15 opposite to the first side surface 13.

The flow guide 150 may be formed of any suitable material such as, for example, metal or a transparent plastic.

The flow speed of liquid fuel in the flow channel 160 can be maintained at a speed that does not allow bubbles to stay in the flow channel 160. Such a speed may be, for example, approximately 15 to 40 cm/sec.

An operation of flowing device according to the embodiment of FIGS. 2-5 will now be described with reference to FIGS. 3A through 5. Liquid fuel that has entered through the fuel inlet 112 passes through the flow channel 160. At this time, the methanol sensor 10 measures the concentration of methanol by irradiating light toward the first surface 11 and receiving the light totally reflected by the first surface 11.

Liquid fuel that has passed through the flow channel 160 enters through the opening 151 into an empty space between the first surface 13 and the housing 110. Next, the liquid fuel is discharged to the outside through the discharge flow line 170 and the fuel outlet 114 after contacting the second side surface 15. The liquid fuel contacts many exterior surfaces of the sensor main body 60 while flowing through the discharge flow line 170 and the flow guide 150. Accordingly, any temperature difference between the first surface 11 and other portions of the sensor main body 60 can be reduced.

Figure 6:
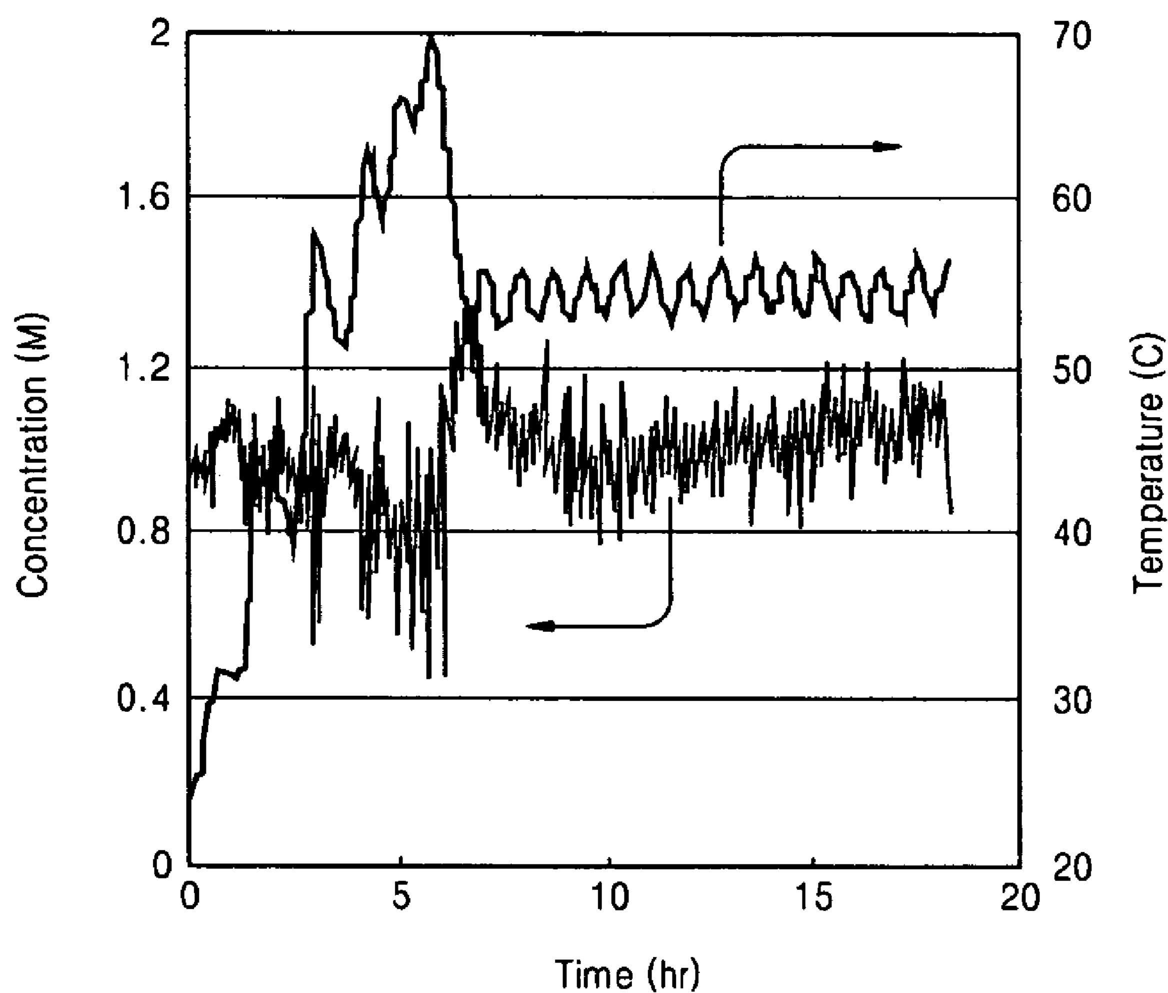
FIG. 6 is a graph showing a test result of the flowing device of FIG. 2.

FIG. 6 is a graph showing a test result of a flowing device according to an embodiment of the present invention. In the test, 1.0M methanol liquid fuel was passed through the flow channel 160 at a flowrate of 40 ml/min. The cross-sectional area of the flow channel 160 was 3.14 $mm^2$. Accordingly, the speed of the liquid fuel was 21 cm/sec. FIG. 6 shows the result of concentration measurements taken for 18 hours. Referring to FIG. 6, at an early stage, concentration changes were observed due to the temperature variations. However, the concentration measurements became uniform as the temperature stabilized. It is believed that the uniformity of measurements was achieved because the rapid flow of liquid fuel inhibited the accumulation of bubbles in the flow channel and because a uniform temperature was maintained in the methanol sensor due to a large contact surface between the liquid fuel and the sensor main body created by the flow guide.

Figure 7:
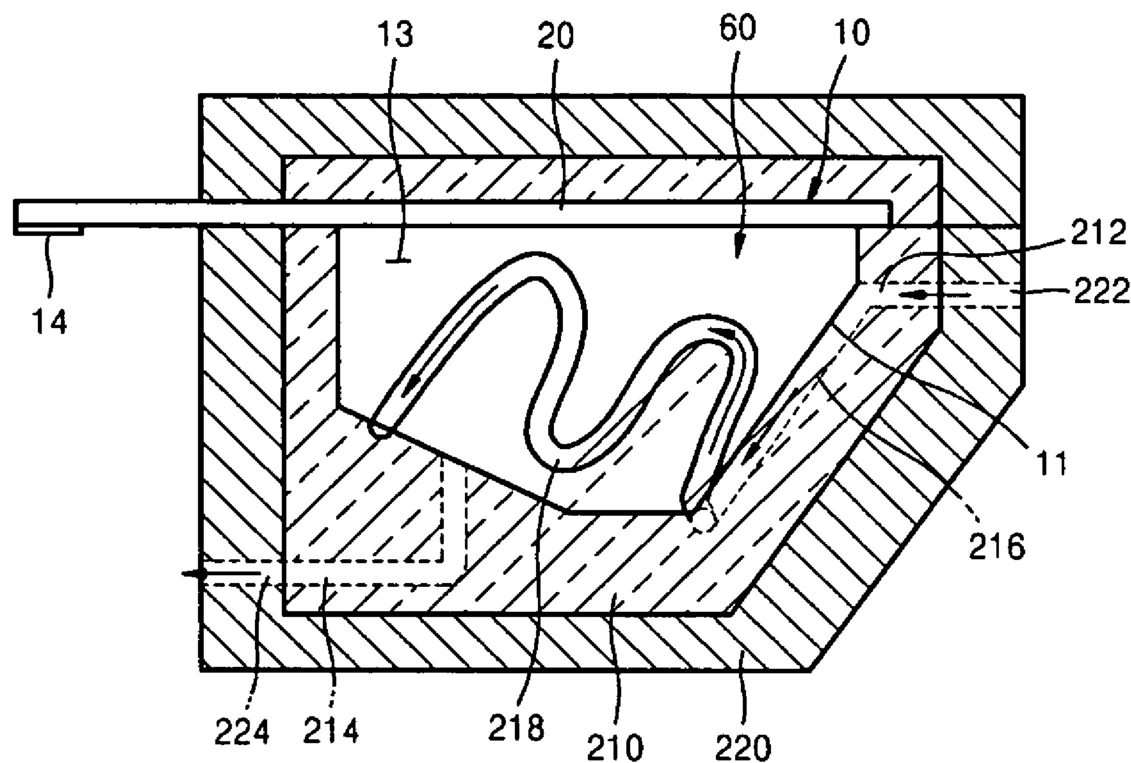
FIG. 7 is a cross-sectional view of a flowing device for an optics-based methanol sensor according to another embodiment of the present invention.

FIG. 7 is a cross-sectional view of a flowing device for an optics-based methanol sensor according to another embodiment of the present invention. Like reference numerals in FIG. 7 denote like elements in FIG. 1, and thus the detailed descriptions thereof are omitted.

The methanol sensor 10 is doubly surrounded by an inner housing 210 and an outer housing 220. As with the previous embodiment, an end of a base plate 20 of the methanol sensor 10 is exposed, and a metal line 14 for electrically connecting the sensor 10 to an outside terminal is formed on the exposed end of the base plate 20. The inner housing 210 and the outer housing 220 include fuel inlets 212 and 222 through which liquid fuel enters and fuel outlets 214 and 224 through which the liquid fuel exits from the inner housing 210 and the outer housing 220.

The inner housing 210 includes a flow channel groove 216 and a flow path, such as, for example, a serpentine groove 218 that contacts the sensor main body 60. As used herein, the term "serpentine groove" refers to any structure that directs liquid fuel along a serpentine or curved path. The flow channel groove 216 contacts the first surface 11 of the methanol sensor 10, and the serpentine groove 218 contacts the first side surface 13 and a second side surface (not shown) of the sensor main body 60. The serpentine groove 218 is connected to the fuel outlet 214. The serpentine groove 218 can ensure a uniform distribution of temperature of the sensor main body 60 of the methanol sensor 10.

The inner housing 210 may be formed of a material having a high thermal conductivity such as, for example, Al, stainless steel, etc., so that the temperature of the sensor main body 60 of the methanol sensor 10 can be kept uniform.

The outer housing 220 may be formed of a material having a low thermal conductivity, such as, for example, a plastic such as PVC, PS, nylon, etc. The plastic keeps the temperature of the inner housing 210 uniform.

An operation of the flowing device shown in FIG. 7 will now be described.

Liquid fuel that has entered through the fuel inlets 212 and 222 passes through the flow channel groove 216. At this time, the methanol sensor 10 measures the concentration of methanol by irradiating light toward the first surface 11 and receiving light totally reflected by the first surface 11.

The liquid fuel that has passed through the flow channel groove 216 is discharged to the outside through the fuel outlets 214 and 224 after contacting the first side surface 13 of the sensor main body 60 through the serpentine groove 218. The liquid fuel may also contact the second side surface through an additional serpentine groove (not shown), which can be a continuation of the serpentine groove 218. The liquid fuel can contact many surfaces of the sensor main body 60 by passing through the serpentine groove 218, and accordingly the presence of the liquid fuel reduces any temperature differences between the first surface 11 and other portions of the sensor main body 60.

The inner housing 210 maintains the uniformity of the temperature of the sensor main body 60 due to its high thermal conductivity, and the outer housing 220 keeps the temperature of the inner housing 210 uniform. The flow speed of liquid fuel in the flow channel groove 216 may be approximately 15 to 40 cm/sec, for example, in order to repress the accumulation of bubbles in the flow channel groove 216. The uniform temperature of the methanol sensor 10 and the repression of bubbles in the flow channel groove 216 enhance the reliability of the concentration measurement of the methanol sensor 10.

As described above, a flowing device for an optics-based methanol sensor according to aspects of the present invention keeps the temperature of the methanol sensor uniform and represses the accumulation of bubbles in a flow channel by controlling the flow speed of liquid fuel in the flow channel, thereby increasing the precision of the methanol sensor.

Although a few embodiments of the present invention have been shown and described, it would be appreciated by those skilled in the art that changes may be made in this embodiment without departing from the principles and spirit of the invention, the scope of which is defined in the claims and their equivalents.

What is claimed is:

1. A flowing device for an optics-based liquid fuel sensor comprising:

an inner housing that surrounds the optics-based liquid fuel sensor;

an outer housing that surrounds the inner housing;

a flow channel in the inner housing formed on a totally reflecting surface of the optics-based liquid fuel sensor;

a fuel inlet that is formed through the inner and outer housings and supplies liquid fuel to the flow channel;

a fuel outlet that is formed through the inner and outer housings and discharges the liquid fuel that has passed through the flow channel to an outside of the outer housing; and a flow path between the flow channel and the fuel outlet such that liquid fuel that has passed through the flow channel contacts an additional surface of the optics-based liquid fuel sensor.

2. The flowing device of claim 1, wherein the optics-based liquid fuel sensor is an optics-based methanol sensor.

3. The flowing device of claim 1, wherein the flow path is a serpentine groove.

4. The flowing device of claim 1, wherein the inner housing is formed of a material having a higher thermal conductivity than a material of a main body of the optics-based liquid fuel sensor.

5. The flowing device of claim 4, wherein the inner housing is formed of a metal.

6. The flowing device of claim 1, wherein the outer housing is formed of a material having a lower thermal conductivity than a material of a main body of the optics-based liquid fuel sensor.

7. The flowing device of claim 6, wherein the outer housing is formed of a plastic material.

8. The flowing device of claim 1, wherein the flow channel accommodates a liquid fuel having a flow speed of 15 to 40cm/sec.

9. A direct liquid feed fuel cell system comprising:

a direct liquid feed fuel cell and an optics-based liquid fuel sensor system that determines a concentration of liquid fuel entering the direct liquid feed fuel cell, wherein the optics-based liquid fuel sensor system comprises an optics-based liquid fuel sensor and the flowing device of claim 1.

10. The direct liquid feed fuel cell system of claim 9, wherein the direct liquid feed fuel cell is a direct methanol fuel cell and the optics-based liquid fuel sensor is an optics-based methanol sensor.

11. A flowing device for an optics-based liquid fuel sensor comprising:

a housing that surrounds the optics-based liquid-fuel sensor;

a flow guide that is disposed between the housing and the optics-based liquid fuel sensor, and comprising a flow channel formed on a totally reflecting surface of the optics-based liquid fuel sensor and an opening between a first side surface of the optics-based liquid fuel sensor and the housing such that liquid fuel that has passed through the flow channel is guided to contact a first side surface of the optics-based liquid fuel sensor;

a fuel inlet that is formed through the housing to supply liquid fuel to the flow channel; and a fuel outlet that is formed through the housing to discharge the liquid fuel that has passed through the flow channel and that has contacted the first side surface of the optics-based liquid fuel sensor to an outside of the housing.

12. The flowing device of claim 11, wherein the optics-based liquid fuel sensor is an optics-based methanol sensor.

13. The flowing device of claim 11, further comprising a discharge flow line installed between the housing and a second side surface opposite to the first side surface of the optics-based liquid fuel sensor, wherein the liquid fuel that has passed through the opening of the flow guide is directed to the fuel outlet through the discharge flow channel.

14. The flowing device of claim 11, wherein the flow channel comprises a groove formed on the flow guide to contact the totally reflecting surface.

15. The flowing device of claim 11, wherein the flow channel accommodates a liquid fuel having a flow speed of 15 to 40cm/sec 15 to 40cm/sec.

16. A direct liquid feed fuel cell system comprising:

a direct liquid feed fuel cell and an optics-based liquid fuel sensor system that determines a concentration of liquid entering the direct liquid feed fuel cell, wherein the optics-based liquid fuel sensor system comprises an optics-based liquid fuel sensor and the flowing device of claim 11.

17. The direct liquid feed fuel cell system of claim 16, wherein the direct liquid feed fuel cell is a direct methanol fuel cell and the optics-based liquid fuel sensor is an optics-based methanol sensor.

18. A method of determining a concentration of a liquid fuel in a water/liquid fuel mixture comprising:

directing the water/liquid fuel mixture along a flow channel formed on a totally reflecting surface of an optics-based liquid fuel sensor at a flow speed sufficient to inhibit an accumulation of bubbles in the flow channel, while irradiating the totally reflecting surface with light and determining a concentration of light reflected from the totally reflecting surface, and directing the water/liquid fuel mixture that has passed through the flow channel along a flow path wherein the water/liquid fuel mixture contacts at least one structural surface of the optics-based liquid fuel sensor so as to equilibrate a temperature of the totally reflecting surface of the optics-based liquid fuel sensor and the at least one structural surface of the optics-based liquid fuel sensor.

19. The method of claim 18, wherein the flow speed of the water/liquid fuel mixture along the flow channel on the totally reflecting surface of the optics-based liquid fuel sensor is 15 to 40cm/sec.

* * * * *